United States Patent [19]

Blum et al.

[11] 4,327,039

[45] Apr. 27, 1982

[54] PROCESS FOR THE PRODUCTION OF 3-AMINO-1-HYDROXYPROPANE-1,1-DIPHOSPHONIC ACID

[75] Inventors: Helmut Blum; Karl-Heinz Worms, both of Dusseldorf, Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 192,733

[22] Filed: Oct. 1, 1980

[30] Foreign Application Priority Data

Oct. 27, 1979 [DE] Fed. Rep. of Germany ....... 2943498

[51] Int. Cl.$^3$ .............................................. C07C 9/38
[52] U.S. Cl. ................................................ 260/502.5
[58] Field of Search ...................... 260/502.5, 502.4 A

[56] References Cited

U.S. PATENT DOCUMENTS 3,361,528 1/1968 Shen ............................ 260/502.4 A
3,366,677 1/1968 Quimby ....................... 260/502.4 A

FOREIGN PATENT DOCUMENTS 2130794 1/1973 Fed. Rep. of Germany .
2702631 7/1978 Fed. Rep. of Germany ... 260/502.5

OTHER PUBLICATIONS

Van Wazer, "Phosphorus and its Compounds", vol. 1, Chemistry, pp. 239, 240, (1958).

*Primary Examiner*—Joseph E. Evans
*Attorney, Agent, or Firm*—Hammond & Littell, Weissenberger and Muserlian

[57] ABSTRACT

A process for the preparation of 3-amino-1-hydroxypropane-1,1-diphosphonic acid having the formula:

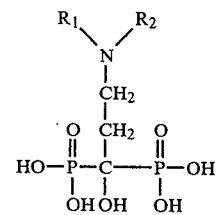

wherein $R_1$ and $R_2$ are selected from the group consisting of hydrogen and lower alkyl, consisting essentially of the steps of reacting a $\beta$-alanine compound selected from the group consisting of $\beta$-alanine and lower alkylated $\beta$-alanine with a phosphonating reactant selected from the group consisting of:
(1) a mixture of phosphorous acid and PCl$_5$, and
(2) a mixture of phosphorous acid, PCl$_3$ and Cl$_2$,
hydrolyzing the reaction mixture, and recovering said 3-amino-1-hydroxypropane-1,1-diphosphonic acid.

2 Claims, No Drawings

PROCESS FOR THE PRODUCTION OF 3-AMINO-1-HYDROXYPROPANE-1,1-DIPHOSPHONIC ACID

BACKGROUND OF THE INVENTION

The invention concerns an improved process for the preparation of 3-amino-1-hydroxypropane-1,1-diphosphonic acid in which the amino group may be substituted by lower alkyl radicals.

The preparation of 3-amino-1-hydroxypropane-1,1-diphosphonic acid by reaction of β-alanine with a mixture of phosphorous trichloride and phosphorous acid in the presence or absence of an organic diluent is known from the German Patent Specification No. 21 30 794. However, yellow-red by-products in the form of amorphous phosphorus-oxygen compounds of unknown structure are formed in this reaction and their separation, particularly in the presence of chlorobenzene, is very costly. Another factor to be considered in the large scale preparations is the dangerously high flammability of these phosphorus compounds.

It is also known that 3-amino-1-hydroxypropane-1,1-diphosphonic acid can be prepared by reacting β-alanine with a mixture of phosphorous acid and $POCl_3$, with subsequent hydrolysis of the reaction mixture, to avoid these disadvantages. Among other drawbacks, however, this process is unsatisfactory with respect to the yields.

OBJECTS OF THE INVENTION

An object of the present invention is the development of a process for the production of 3-amino-1-hydroxypropane-1,1-diphosphonic acid in good yields with greatly decreased formation of phosphorus-oxygen by-products.

Another object of the present invention is the development of a process for the preparation of 3-amino-1-hydroxypropane-1,1-diphosphonic acid having the formula:

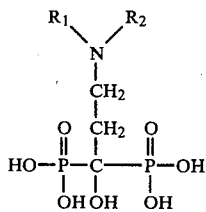

wherein $R_1$ and $R_2$ are selected from the group consisting of hydrogen and lower alkyl, consisting essentially of the steps of reacting a β-alanine compound selected from the group consisting of β-alanine and lower alkylated β-alanine with a phosphonating reactant selected from the group consisting of:

(1) a mixture of phosphorous acid and $PCl_5$, and
(2) a mixture of phosphorous acid, $PCl_3$ and $Cl_2$, hydrolyzing the reaction mixture, and recovering said 3-amino-1-hydroxypropane-1,1-diphosphonic acid.

These and other objects of the present invention will become more apparent as the description thereof proceeds.

DESCRIPTION OF THE INVENTION

It has now been found that the previously employed methods to produce 3-amino-1-hydroxypropane-1,1-diphosphonic acid can be improved by the use of the process described below. The new process is characterized by the fact that β-alanine, in which the amino groups may be substituted by lower alkyl radicals, is reacted with a mixture of phosphorous acid and $PCl_5$ or with a mixture of phosphorous acid, $PCl_3$ and chlorine, and the reaction mixture is then hydrolyzed.

More particularly, the present invention relates to a process for the preparation of 3-amino-1-hydroxypropane-1,1-diphosphonic acid having the formula:

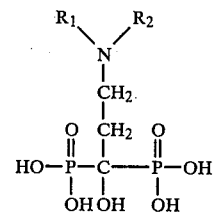

wherein $R_1$ and $R_2$ are selected from the group consisting of hydrogen and lower alkyl, consisting essentially of the steps of reacting a β-alanine compound selected from the group consisting of β-alanine and lower alkylated β-alanine with a phosphonating reactant selected from the group consisting of:

(1) a mixture of phosphorous acid and $PCl_5$, and
(2) a mixture of phosphorous acid, $PCl_3$ and $Cl_2$, hydrolyzing the reaction mixture, and recovering said 3-amino-1-hydroxypropane-1,1-diphosphonic acid.

The starting product is particularly β-alanine. Other β-alanines, which have their hydrogen atoms located on the amino group partially or completely replaced by lower alkyl radicals, such as methyl, ethyl or propyl, also may be used as starting products.

It is advantageous to use a substantially stoichiometric to an excess of the phosphorous acid and $PCl_5$, such as 1 to 1.5 mols of $H_3PO_3$ and 1 to 1.5 mols of $PCl_5$ per mol of β-alanine. As was further discovered, $PCl_5$ also may be replaced by a mixture of $PCl_3$ and $Cl_2$. When the process is performed in the last-mentioned manner, it is advantageous to prepare first a mixture of β-alanine, $H_3PO_3$ and $PCl_3$ at a molar ratio of substantially 1:1:1, and to then inject a corresponding amount of chlorine gas.

If desired, diluents, preferably chlorinated hydrocarbons, such as chlorobenzene, tetrachloroethane, tetrachloroethylene, trichloroethylene or carbon tetrachloride may be used to carry out the reaction. The reaction generally is performed at temperatures between 80° C. and 130° C., preferably at about 100° C. Then the reaction mixture is hydrolyzed by the addition of water, using advantageously enough $H_2O$ barely to dissolve the reaction product. The hydrolysis is advantageously carried out at elevated temperatures, such as from 30° C. to 100° C. The desired product then crystallizes from the aqueous solution, after separation of the solvent, if present. The yield can be increased by the separation of the mother liquor and the addition of alcohol or acetone thereto.

The 3-amino-1-hydroxypropane-1,1-diphosphonic acids obtained, which may be alkylated at the nitrogen atom, if desired, are good complexing agents for heavy metals and alkaline earth metals that are also active in amounts below the stoichiometric quantity. Consequently, they can be used in cleaning and water treatment compositions.

The following specific embodiments are illustrative of the practice of the invention without being limitative thereto.

EXAMPLE 1

A suspension of 1.5 mols of $PCl_5$ in 500 ml of chlorobenzene was prepared and then mixed with 1.5 mols of $H_3PO_3$. The exothermic reaction produced a clear solution with the formation of HCl. After cooling to room temperature, 1 mol of β-alanine was added thereto. After stirring for 15 minutes, the mixture was heated to 100° C. within one hour and kept at this temperature for three hours. The reaction mixture obtained after this time was hydrolyzed with 600 ml $H_2O$, leading to the complete solution of the practically solid product. After the separation of the chlorobenzene phase, pure 3-amino-1-hydroxypropane-1,1-diphosphonic acid was obtained by crystallization from the cooled solution in a yield of 65.1%. The yield can be increased by mixing mother liquor with methanol.

EXAMPLE 2

A suspension of 0.345 mol of $PCl_5$ in 120 ml of chlorobenzene was first mixed with 0.345 mol of $H_3PO_3$ and, after cooling, with 0.23 mol of N,N-diethylaminopropionic acid. The mixture was stirred for ten minutes and then slowly heated to 100° C., and the reaction mixture was then kept at this temperature for another three hours. Thereafter, the chlorobenzene phase was decanted, and the pasty reaction product was hydrolyzed with about 80 ml $H_2O$ at 100° C.

The 3-(N,N-diethylamine)-1-hydroxypropane-1,1-diphosphonic acid was precipitated by adding the solution dropwise into an alcohol/acetone mixture (2/1).

EXAMPLE 3

A mixture of β-alanine, $H_3PO_3$ and $PCl_3$ in a molar ratio of 1:1:1 in 500 ml of chlorobenzene, was prepared. Then chlorine gas was added at room temperature for two and a half hours. The reaction mixture was thereafter heated to 100° C. and kept at this temperature for four hours. After cooling, the hydrolysis was performed at 50° C. with 400 ml of $H_2O$. The chlorobenzene phase was separated and the 3-amino-1-hydroxypropane-1,1-diphosphonic acid was crystallized by further cooling to 0° to 10° C. The yield was 72%.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of 3-amino-1-hydroxypropane-1,1-diphosphonic acid consisting essentially of the steps of reacting β-alanine with a substantially stoichiometric to an excess amount with respect to said β-alanine of a phosphonating reactant selected from the group consisting of:

(1) a mixture of phosphorous acid and $PCl_5$, and
    (2) a mixture of phosphorous acid, $PCl_3$ and $Cl_2$, under anhydrous conditions in the presence of a chlorinated hydrocarbon diluent, at a temperature of from 80° C. to 130° C., hydrolyzing the reaction mixture, and recovering said 3-amino-1-hydroxypropane-1,1-diphosphonic acid.

2. The process of claim 1 wherein said phosphonating reactant is employed in about 1 to 1.5 times the molar amount of said β-alanine compound.

* * * * *